US008455112B2

(12) United States Patent
Boerner et al.

(10) Patent No.: US 8,455,112 B2
(45) Date of Patent: Jun. 4, 2013

(54) ORGANOMETALLIC COMPLEXES WHICH EMIT IN THE RED TO GREEN SPECTRAL REGION AND THEIR USE IN OLEDS

(75) Inventors: Herbert Friedrich Boerner, Aachen (DE); Hans-Peter Loebl, Monschgau-Imgenbroich (DE); Josef Salbeck, Kaufungen (DE); Elena Popova, Kassel (DE)

(73) Assignee: BASF SE, Ludwigshafen (DE)

( * ) Notice: Subject to any disclaimer, the term of this patent is extended or adjusted under 35 U.S.C. 154(b) by 593 days.

(21) Appl. No.: 12/594,429

(22) PCT Filed: Apr. 4, 2008

(86) PCT No.: PCT/EP2008/054087
§ 371 (c)(1),
(2), (4) Date: Dec. 16, 2009

(87) PCT Pub. No.: WO2008/122603
PCT Pub. Date: Oct. 16, 2008

(65) Prior Publication Data
US 2010/0127215 A1    May 27, 2010

(30) Foreign Application Priority Data

Apr. 4, 2007    (EP) .................................... 07105649

(51) Int. Cl.
*C09K 11/06*    (2006.01)
*H01L 51/54*    (2006.01)

(52) U.S. Cl.
USPC ................. 428/690; 428/917; 546/4; 546/10; 548/103; 548/402; 544/179; 544/181; 544/225; 313/504; 257/E51.044

(58) Field of Classification Search
None
See application file for complete search history.

(56) References Cited

U.S. PATENT DOCUMENTS

| 2002/0034656 | A1  | 3/2002 | Thompson et al. |
| 2005/0025995 | A1* | 2/2005 | Cheng et al. .................. 428/690 |
| 2006/0036097 | A1  | 2/2006 | Qiu et al. |
| 2010/0109515 | A1* | 5/2010 | Boerner et al. ............... 313/504 |

FOREIGN PATENT DOCUMENTS

| JP | 9-176629 A | * | 7/1997 |
| WO | 2005 113704 |   | 12/2005 |
| WO | 2006 093466 |   | 9/2006 |

OTHER PUBLICATIONS

Machine translation of JP 09-176629 (Jul. 1997).*
Velusamy, M. et al., "Synthesis, structure and electroluminescent properties of cyclometalated iridium complexes possessing sterically hindered ligands", Dalton Transactions, pp. 3025-3034 (Mar. 30, 2007) XP002490863.
Baldo, M. A., et al. "Very High-efficiency Green Organic Light-Emitting Devices Based on Electrophosphorescence", Appl. Phys. Lett., vol. 75, No. 1, pp. 4-6 (Jul. 5, 1999).

* cited by examiner

*Primary Examiner* — Marie R. Yamnitzky
(74) *Attorney, Agent, or Firm* — Oblon, Spivak, McClelland, Maier & Neustadt, L.L.P.

(57) ABSTRACT

Organometallic complexes which bear at least one ligand which has a unit having a triplet energy of at least 22 000 $cm^{-1}$, a process for preparing the organometallic complexes, a mixture comprising at least one of these organometallic complexes, the use of the organometallic complexes or of the mixture in organic light-emitting diodes, the organometallic complexes preferably being used as emitter materials, and specific nitrogen- or phosphorus-substituted triphenylene derivatives and a process for their preparation, the organometallic complex including a monoanionic bidentate ligand of formula (IIa)

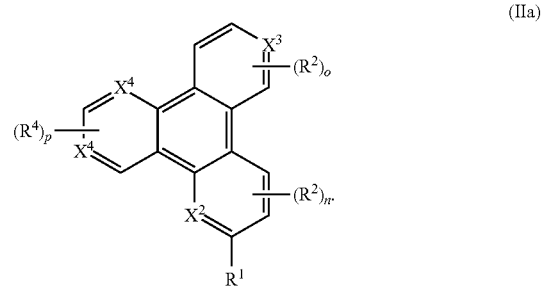

(IIa)

10 Claims, No Drawings

ORGANOMETALLIC COMPLEXES WHICH EMIT IN THE RED TO GREEN SPECTRAL REGION AND THEIR USE IN OLEDS

CROSS-REFERENCE TO RELATED APPLICATIONS

This application is a National Stage of PCT/EP08/054,087 filed Apr. 4, 2008 and claims the benefit of EP 07105649.3 filed Apr. 4, 2007.

The present invention relates to organometallic complexes which bear at least one ligand which has a unit having a triplet energy of at least 22 000 cm$^{-1}$, to a process for preparing the organometallic complexes, to a mixture comprising at least one inventive organometallic complex, to the use of the organometallic complexes or of the mixture in organic light-emitting diodes, the organometallic complexes preferably being used as emitter materials, and to specific nitrogen- or phosphorus-substituted triphenylene derivatives and to a process for their preparation.

Organic light-emitting diodes (OLEDs) exploit the property of materials to emit light when they are excited by electrical current. OLEDs are of particular interest as an alternative to cathode ray tubes and liquid-crystal displays for the production of flat visual display units and as a particularly efficient light source. Owing to the very compact design and the intrinsically low power consumption, devices comprising OLEDs are suitable especially for mobile applications, for example for applications in cellphones, laptops, digital cameras, etc.

The basic principles of the way in which OLEDs function and suitable constructions (layers) of OLEDs are known to those skilled in the art and are specified, for example, in WO 2005/113704 and the literature cited therein. The light-emitting materials (emitters) used may, as well as fluorescent materials (fluorescence emitters), be phosphorescent materials (phosphorescence emitters). The phosphorescence emitters are typically organometallic complexes which, in contrast to the fluorescence emitters which exhibit singlet emission, exhibit triplet emission (triplet emitters) (M. A. Baldow et al., Appl. Phys. Lett. 1999, 75, 4 to 6).

For quantum-mechanical reasons, when the triplet emitters (phosphorescence emitters) are used, up to four times the quantum efficiency, energy efficiency and power efficiency are possible. In order to implement the advantages of the use of the organometallic triplet emitters in practice, it is desirable to provide emitter materials which are notable for a good stability, a high luminescence efficiency, a high color purity and suitable solubilities.

The prior art proposes numerous different materials for use as emitter materials in OLEDs. Among the proposed materials are also transition metal complexes which exhibit phosphorescence.

For instance, US 2002/0034656 A1 relates to a light-emitting layer of an OLED, which comprises a phosphorescent organometallic compound, for increasing the quantum efficiency of the OLED. Particularly suitable emitter materials are, according to US 2002/0034656 A1, phosphorescent organometallic complexes of platinum, iridium or osmium, very particular preference being given to using cyclometalated phosphorescent platinum, iridium or osmium complexes. Examples of suitable phosphorescent transition metal complexes mentioned are Ir(ppy)$_3$ and platinum(II) complexes with bis[2-(2-phenyl)pyridinato-N,C2], bis[2(2'-thienyl)pyridinato-N,C3] or bis[benzo-(h)quinolinato-N,C].

In addition, known emitter materials are suitable phosphorescent Ir complexes of the general formulae

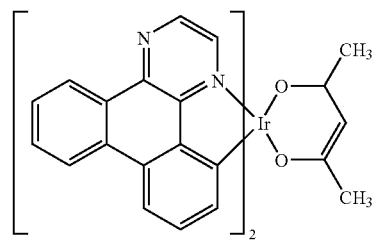

ADS 075RE

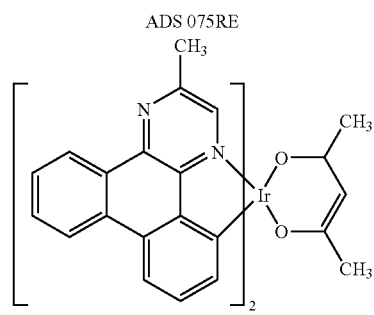

ADS 076RE from American Dyesource (www.adsdyes.com) (compounds ADS 075RE and ADS 076RE). However, these complexes exhibit a strong red shift of the emission.

It is an object of the present invention to provide emitter materials for OLEDs, which exhibit a good thermal stability and are suitable for producing OLEDs with good efficiency and high color purity.

This object is achieved by the provision of organometallic complexes of the general formula (I)

$$M[L_1]_q[L_2]_r[L_3]_s \qquad (I)$$

in which

M is a metal atom;

$L_1$ is a ligand which may be uncharged, mono- or dianionic and mono- or bidentate and is preferably a monoanionic bidentate ligand based on a compound of the formula (II)

(II)

in which:

$R^1$ is an N-comprising radical,

is a unit having a triplet energy of at least 22 000 cm$^{-1}$;

$L_2$ is a mono- or dianionic ligand which may be mono- or bidentate;

$L_3$ is an uncharged mono- or bidentate ligand;

q is the number of ligands $L_1$, where q is 1, 2 or 3 and the ligands $L_1$, when q>1, may be the same or different;

r is the number of ligands $L_2$, where r is from 0 to 4 and the ligands $L_2$, when r>1, may be the same or different;

s is the number of ligands $L_3$, where s is from 0 to 4 and the ligands $L_3$, when s>1, may be the same or different;

where the sum of q+r+s depends on the oxidation stage and coordination number of the metal M used and on the density of the ligands $L_1$, $L_2$ and $L_3$ and also on the charge of the ligands $L_1$ and $L_2$.

The organometallic complexes of the formula (I) according to the present invention feature outstanding efficiencies when used in OLEDs, especially because they may be present in high concentration in the light-emitting layer of an OLED, and it is possible to suppress the formation of dimers and hence the quenching of the excited state.

Furthermore, when the inventive organometallic complexes are used, emissions with high color purity can be achieved, and the organometallic complexes according to the present invention have a high thermal stability.

The inventive organometallic complexes comprise at least one unit having a triplet energy of at least 22 000 cm$^{-1}$ (determined by a low-temperature photoluminescence measurements), preferably having a triplet energy of from 22 000 cm$^{-1}$ to 28 230 cm$^{-1}$, more preferably from 22 000 to 25 000 cm$^{-1}$. In the context of the present application, the triplet energy is understood to mean the energy of the first triplet level.

The ligand $L_1$ in the inventive organometallic complexes of the formula (I) preferably has a triplet energy of at least 16 000 cm$^{-1}$, preferably from 16 000 cm$^{-1}$ to 19 500 cm$^{-1}$, more preferably from 16 000 to 18 500 cm$^{-1}$.

The inventive organometallic complexes generally exhibit electroluminescence in the visible range of the electromagnetic spectrum, preferably from 400 nm to 800 nm, more preferably from 450 nm to 800 nm, most preferably from 490 nm to 750 nm.

The $R^1$ radical in the ligand $L_1$ based on a compound of the formula (II) is, in accordance with the invention, an N-comprising radical. The radical is preferably a heterocyclic radical which may be substituted or unsubstituted, more preferably an N-heterocyclic radical which comprises at least one nitrogen atom. Most preferably, the $R^1$ radical is a mono-, bi- or tricyclic heteroaromatic radical which may be substituted or unsubstituted. The $R^1$ radical is very especially preferably a pyridyl or benzothiazyl radical or a triazolyl radical, an isoxazolyl radical or a pyrazolyl radical, which may be substituted or unsubstituted. Suitable substituents of the $R^1$ radical are the suitable substituents mentioned below. In a very particularly preferred embodiment, the $R^1$ radical is unsubstituted, i.e. all substitutable positions of the $R^1$ radical are substituted by hydrogen atoms.

The unit having a triplet energy of at least 22 000 cm$^{-1}$ in the ligand $L_1$ based on a compound of the formula (II) may be any unit which is known to those skilled in the art, has the triplet energy mentioned and is suitable for forming organometallic complexes. The unit is preferably a unit based on triphenylene or a derivative thereof, such that the compound of the formula (II), on which the ligand $L_1$ is based, preferably has the general formula (IIa)

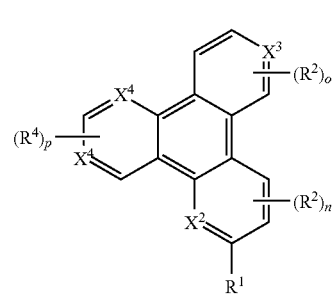

(IIa)

in which the $R^1$ radical is as already defined above and the further radicals and indices are each defined as follows:

$R^2$, $R^3$, $R^4$ are each independently $C_1$-$C_{20}$-alkyl, $C_0$-$C_{20}$-alkylene-$C_3$-$C_{18}$-cycloalkyl, $C_0$-$C_{20}$-alkyleneheterocycloalkyl having from 3 to 18 ring atoms, $C_0$-$C_{20}$-alkylene-$C_1$-$C_{20}$-alkoxy, $C_0$-$C_{20}$-alkylene-$C_6$-$C_{18}$-aryloxy, $C_0$-$C_{20}$-alkylene-$C_6$-$C_{18}$-aryl, $C_0$-$C_{20}$-alkyleneheteroaryl having from 5 to 18 ring atoms, where the aforementioned radicals may be substituted by hydroxyl, halogen, pseudohalogen, alkyl, cycloalkyl, heterocycloalkyl, aryl, heteroaryl, amino, —C(O)R', —C(O)OR'', —OC(O)R''', —OC(O)OR'''', where R', R'', R''' and R'''' are each independently hydrogen, alkyl, cycloalkyl, heterocycloalkyl, aryl, heteroaryl or amino, or be unsubstituted; hydroxyl, halogen, pseudohalogen, phosphonate, phosphate, phosphine, phosphine oxide, phosphoryl, sulfonyl, sulfonate, sulfate, amino, polyether, silyl-$C_1$-$C_{20}$-alkyl, silyl-$C_0$-$C_{20}$-alkylene-$C_6$-$C_{18}$-aryl, silyl-$C_0$-$C_{20}$-alkylene-$C_1$-$C_{20}$-alkoxy, —C(O)R', —C(O)OR'', —OC(O)R''', —OC(O)OR'''', where R', R'', R''' and R'''' are each independently hydrogen, alkyl, cycloalkyl, heterocycloalkyl, aryl, heteroaryl or amino;

$R^2$, $R^3$ and $R^4$ are preferably each independently $C_1$-$C_{20}$-alkyl, preferably $C_1$-$C_8$-alkyl; $C_0$-$C_{20}$-alkylene-$C_3$-$C_{18}$-cycloalkyl, preferably $C_0$-$C_6$-alkylene-$C_5$-$C_6$-cycloalkyl; $C_0$-$C_{20}$-alkyleneheterocycloalkyl having 3-18 ring atoms, preferably $C_0$-$C_6$-alkyleneheterocycloalkyl having 5 or 6 ring atoms; $C_0$-$C_{20}$-alkylene-$C_1$-$C_{20}$-alkoxy, preferably $C_0$-$C_6$-alkylene-$C_1$-$C_8$-alkoxy; $C_0$-$C_{20}$-alkylene-$C_6$-$C_{18}$-aryloxy, preferably $C_0$-$C_8$-alkylene-$C_6$-aryloxy; $C_0$-$C_{20}$-alkylene-$C_6$-$C_{18}$-aryl, preferably $C_0$-$C_6$-alkylene-$C_6$-aryl; $C_0$-$C_{20}$-alkyleneheteroaryl having 5-18 ring atoms, preferably $C_0$-$C_6$-alkyleneheteroaryl having 5 or 6 ring atoms, where the radicals mentioned may be unsubstituted or substituted, preferred substituents being alkyl, preferably $C_1$-$C_8$-alkyl; alkoxy, preferably $C_1$-$C_8$-alkoxy; halogen, preferably F, Cl, Br, I, more preferably F, Cl; or pseudohalogen, preferably CN, SCN, OCN, $N_3$, CNO, SeCN, more preferably CN, SCN;

o is from 0 to 3, where the $R^3$ radicals, where o>1, may be the same or different;

n, p are each independently from 0 to 2, where the $R^2$ or $R^4$ radicals, when n or p>1, may be the same or different;

$X^2$ is N, CH or $CR^2$;

$X^3$ is N, CH or $CR^3$;

$X^4$ are each independently N, CH or $CR^4$.

In the context of the present application, the terms alkyl, alkylene, cycloalkyl, heterocycloalkyl, alkoxy, aryloxy, aryl, heteroaryl, halogen, pseudohalogen, amino, phosphonate, phosphate, phosphine, phosphine oxide, phosphoryl, sulphonyl, sulfonate, sulfate, polyether, silylalkyl, silylalkylenearyl and silylalkylenealkoxy are generally each defined as follows, particularly preferred definitions being specified in the specific definitions of the individual radicals:

Alkyl is understood to mean a radical having from 1 to 20 carbon atoms, preferably from 1 to 10 carbon atoms, more preferably from 1 to 8 carbon atoms, in the longest alkyl chain. This alkyl radical may be branched or unbranched and may optionally be interrupted by one or more heteroatoms, e.g. Si, N, or S, preferably N, O or S. In addition, the alkyl radical may be substituted by one or more substituents specified for the aryl substituent specified below. The alkyl radicals are more preferably selected from the group consisting of methyl, ethyl, isopropyl, n-propyl, n-butyl, sec-butyl, isobutyl, tert-butyl, and also $CF_3$.

A cycloalkyl radical is understood to mean a cyclic alkyl radical having a base skeleton of from three to 18 carbon atoms, preferably from 5 to 8 carbon atoms, more preferably 5 or 6 carbon atoms. Suitable base skeletons are, for example, cyclopentyl or cyclohexyl. The base skeleton of the cycloalkyl radical may be unsubstituted (i.e. all carbon atoms which are substitutable bear hydrogen atoms), or be substituted at one, more than one or all substitutable positions of the base skeleton. Suitable substituents are the substituents specified below for the aryl radicals. Particularly preferred cycloalkyl radicals are cyclohexyl and cyclopentyl.

A heterocycloalkyl radical is understood to mean a radical having from 3 to 18 ring atoms in the base skeleton, preferably 5 or 6 ring atoms. In addition, the heterocycloalkyl radical comprises at least one heteroatom selected from the group consisting of N, O and S. The heterocycloalkyl radical may be substituted at one, more than one or all substitutable positions of the base skeleton. Suitable substituents are the substituents specified for the aryl radicals.

Aryl is understood to mean a radical having a base skeleton of from 6 to 18, preferably from 6 to 10, more preferably 6 carbon atoms, which is formed from an aromatic ring or a plurality of fused aromatic rings. Suitable base skeletons are, for example, phenyl, naphthyl, anthracenyl or phenanthrenyl. This base skeleton may be unsubstituted (i.e. all carbon atoms which are substitutable bear hydrogen atoms) or be substituted at one, more than one or all substitutable positions of the base skeleton. Suitable substituents are, for example, the aforementioned alkyl radicals, aryl radicals, preferably $C_6$-aryl radicals, which may in turn be substituted or unsubstituted, heteroaryl radicals, preferably heteroaryl radicals which comprise at least one nitrogen atom, more preferably pyridyl radicals or groups with donor or acceptor action. Suitable groups with donor or acceptor action are specified below. Most preferably, the aryl radicals bear substituents selected from the group consisting of methyl, F, Cl, CN, aryloxy and alkoxy. The aryl radical is preferably a $C_6$-$C_{18}$-aryl radical, more preferably a $C_6$-$C_{10}$-aryl radical, most preferably a $C_6$-aryl radical, which is substituted by none, one or two of the aforementioned substituents, where, in the case of the $C_6$-aryl radical, the one substituent is arranged in the ortho-, meta- or para-position to the further bonding site of the aryl radical, and—in the case of two substituents—they may each be arranged in the meta-position or ortho-position to the further bonding site of the aryl radical, or one radical is arranged in the ortho-position and one radical in the meta-position, or one radical in the ortho- or meta-position and the further radical in the para-position.

A heteroaryl radical is understood to mean a radical which has from 5 to 18 ring atoms, preferably 5 or 6 ring atoms. At least one of the ring atoms is a heteroatom, preferred heteroatoms being selected from the group consisting of N, O and S. The heteroaryl radical preferably has one or two heteroatoms. The base skeleton is more preferably selected from carbazole, pyridine, pyrrole, furan, pyrazole, imidazole and thiophene. The base skeleton may be substituted at one, more than one or all substitutable positions of the base skeleton. Suitable substituents are the same as have already been specified for the aryl group.

An alkoxy group is understood to mean an O-alkyl group, where the alkyl radical may be defined as specified above. One example of a preferred alkoxy group is OMe.

An aryloxy group is understood to mean an O-aryl group, suitable aryl groups being specified above. One example of a suitable aryloxy group is a phenoxy group.

The expression "$C_0$-$C_{20}$-alkylene" is understood to mean that the corresponding radicals or groups may be bonded directly to the base skeleton ($C_0$-alkylene) or may be bonded to the base skeleton via an alkylene group having from 1 to 20 carbon atoms, preferably from 1 to 10, more preferably from 1 to 6, most preferably 1 or 2 carbon atoms ($C_1$-$C_{20}$-alkylene, preferably $C_1$-$C_{10}$-alkylene, more preferably $C_1$-$C_6$-alkylene, most preferably $C_1$-$C_2$-alkylene). The alkylene radical corresponds to the aforementioned alkyl radicals with the difference that the alkylene radical has two bonding sites to further groups. For example, preferred $C_0$-$C_{20}$-alkylene-$C_6$-$C_{18}$-aryl radicals are benzyl radicals.

In the context of the present application, a group having donor or acceptor action is understood to mean the following groups:

Groups having donor action are understood to mean groups which have a +I and/or +M effect, and groups having acceptor action are understood to mean groups which have a −I and/or −M effect. Suitable groups having donor or acceptor action are halogen radicals, preferably F, Cl, Br, I, more preferably F, Cl, alkoxy radicals, aryloxy radicals, carbonyl radicals, ester radicals, both oxycarbonyl and carbonyloxy, amine radicals, amide radicals, $CH_2F$ groups, $CHF_2$ groups, $CF_3$ groups, CN groups, thio groups, sulfonic acid groups, sulfonic ester groups, boronic acid groups, boronic ester groups, phosphonic acid groups, phosphonic ester groups, phosphine radicals, sulfoxide radicals, sulfonyl radicals, sulfide radicals, nitro groups, OCN, borane radicals, silyl groups, stannate radicals, imino groups, hydrazine radicals, hydrazole radicals, oxime radicals, nitroso groups, diazo groups, phosphine oxide groups, hydroxyl groups or SCN groups. Very particular preference is given to F, Cl, CN, aryloxy and alkoxy.

Pseudohalogen is understood to mean a group selected from CN, SCN, OCN, $N_3$, CNO and SeCN, preferably CN or SCN.

Halogen is understood to mean a group selected from F, Cl, Br and I, preferably F or Cl.

The expression "amino" is an —$NR_2$ group in which each R radical is selected independently from hydrogen, $C_1$-$C_6$-alkyl, $C_1$-$C_6$-alkylene-$C_6H_6$ and $C_6$-$C_{18}$-aryl, where the two R radicals may additionally, together with the nitrogen atom, form a 4- to 6-membered, preferably 5- to 6-membered, heterocyclic ring which may optionally be substituted by $C_1$-$C_6$-alkyl radicals, preferably $C_1$-$C_6$-alkyl, benzyl or phenyl.

Phosphonate is understood to mean —$P(O)(OR)_2$ groups in which the R radicals are each selected independently from hydrogen, alkyl and aryl, preferably hydrogen, $C_1$-$C_6$-alkyl, phenyl and benzyl. In addition, the R radicals may be a cation, e.g. $Na^+$, $K^+$, $Mg^{2+}$ and $Ca^{2+}$.

Phosphate is understood to mean —$OP(O)(OR)_2$ in which the R radicals are each independently hydrogen, alkyl or aryl, preferably hydrogen, $C_1$-$C_6$-alkyl, phenyl or benzyl. In addition, the R radicals may be a cation selected from $Na^+$, $K^+$, $Mg^{2+}$ and $Ca^{2+}$.

Phosphine is understood to mean $—P(R_2)$ in which the R radicals are each independently hydrogen, alkyl or aryl, preferably hydrogen, $C_1$-$C_6$-alkyl, phenyl or benzyl.

Phosphine oxide is understood to mean $—P(O)R_2$ in which the R radicals are each independently hydrogen, alkyl, aryl or amino, preferably hydrogen, $C_1$-$C_6$-alkyl, phenyl, benzyl or $—NR'_2$ in which R' are each independently hydrogen, alkyl or aryl, preferably hydrogen, $C_1$-$C_6$-alkyl, phenyl or benzyl.

Sulfonyl is understood to mean $—S(O)_2R$ in which R is hydrogen, alkyl, aryl or amino, preferably hydrogen, $C_1$-$C_6$-alkyl, phenyl, benzyl or $—NR'_2$ in which R' are each independently hydrogen, alkyl or aryl, preferably hydrogen, $C_1$-$C_6$-alkyl or benzyl.

Sulfonate is understood to mean $—S(O)_2OR$ in which R is hydrogen, alkyl or aryl, preferably hydrogen, $C_1$-$C_6$-alkyl, phenyl or benzyl. In addition, R may be a cation selected from $Na^+$, $K^+$, $Mg^{2+}$ or $Ca^{2+}$.

Sulfate is understood to mean $—OS(O)_2OR$ in which R is hydrogen, alkyl or aryl, preferably hydrogen, $C_1$-$C_6$-alkyl, phenyl or benzyl. In addition, R may be a cation selected from $Na^+$, $K^+$, $Mg^{2+}$ or $Ca^{2+}$.

A polyether radical is understood to mean a group selected from the $—(O—CHR)_n—OH$ and $—(O—CH_2—CHR)_n—H$ groups, where R is selected independently from hydrogen, alkyl, aryl, halogen and n is from 1 to 250.

Silyl-$C_1$-$C_{20}$-alkyl is understood to mean an $SiR_3$ group where the R radicals are each hydrogen or alkyl, preferably $C_1$-$C_6$-alkyl or hydrogen.

Silyl-$C_0$-$C_{20}$-alkylene-$C_6$-$C_{18}$-aryl is understood to mean $—SiR_3$ groups where R is selected independently from aryl, preferably $C_6$-$C_{18}$-aryl, more preferably phenyl, where the aryl group is bonded directly to the Si ($C_0$-alkylene), and $C_1$-$C_{20}$-alkylenearyl groups, preferably $C_1$-$C_{20}$-alkylene-$C_6$-$C_{18}$-aryl, more preferably $C_1$-$C_6$-alkylenephenyl.

A silyl-$C_0$-$C_{20}$-alkylene-$C_1$-$C_{20}$-alkoxy group is understood to mean an $—Si(OR)_3$ group where a $C_0$-alkylene group is present, where the R radical is a $C_1$-$C_{20}$-alkyl radical, preferably a $C_1$-$C_6$-alkyl radical. In addition, the group mentioned is understood to mean an $—Si—C_1$-$C_{20}$-alkylene-$C_1$-$C_{20}$-alkoxy group, preferably an $—Si—C_1$-$C_6$-alkylene-$C_1$-$C_6$-alkoxy group.

In the $—C(O)R'$, $—C(O)R''$, $—OC(O)R'''$, $—C(O)OR''''$ groups, R', R'', R''' and R'''' are each independently defined as hydrogen, alkyl, cycloalkyl, heterocycloalkyl, aryl, heteroaryl or amino, preferably hydrogen, $C_1$-$C_6$-alkyl, $C_3$-$C_8$-cycloalkyl, heterocycloalkyl having from three to eight ring atoms, $C_6$-$C_{18}$-aryl, preferably phenyl, heteroaryl having from 5 to 18 ring atoms or amino as defined above.

A bidentate ligand is understood to mean a ligand which is coordinated to the metal atom M at two points.

A monodentate ligand is understood to mean a ligand which is coordinated to the metal atom M at one point on the ligand.

Depending on the coordination number of the metal M used and the nature and number of the ligands $L_1$, $L_2$ and $L_3$ used, it is possible for different isomers of the corresponding metal complexes to be present with the same transition metal M and same nature and number of ligands used. The present invention relates in each case to individual isomers of the transition metal complexes of the formula (I) and also mixtures of different isomers in any desired mixing ratio. In general, the different isomers of the transition metal complexes of the formula (I) may be separated by processes known to those skilled in the art, for example by chromatography, sublimation or crystallization.

In the compounds of the formula (IIa), the indices n, o and p may each be 0, 1, 2 or 3 (index o) or 0, 1 or 2 (indices n and p). In the case that the indices n, o and p are 0, the corresponding substitutable positions of the triphenylene skeleton or of a derivative thereof are substituted by hydrogen atoms.

Preferred embodiments of the $R^2$, $R^3$ and $R^4$ radicals have been specified above. $R^2$, $R^3$ and $R^4$ are more preferably each $C_1$-$C_4$-alkyl, for example methyl, ethyl, n-propyl, i-propyl, n-butyl, sec-butyl, i-butyl or tert-butyl, halogen-substituted $C_1$-$C_4$-alkyl, preferably F-substituted alkyl, for example $CF_3$, $C_1$-$C_4$-alkoxy, for example OMe, OEt, OnPr, OiPr, OnBu, OsecBu, OiBu, OtertBu, halogen, preferably F or pseudohalogen, preferably CN.

The $R^2$, $R^3$ and $R^4$ radicals in the $X^2$, $X^3$ and $X^4$ groups each independently have the definitions specified above for the $R^2$, $R^3$ and $R^4$ radicals.

In a preferred embodiment of the present invention, the radicals and indices in the triphenylene derivatives of the formula (II) are each defined as follows:

$R^1$ is an N-comprising radical, preferably a heterocyclic radical which may be substituted or unsubstituted, more preferably an N-heterocyclic radical comprising at least one nitrogen atom, most preferably a mono-, bi- or tricyclic heteroaromatic radical which may be substituted or unsubstituted, very especially preferably a pyridyl or benzothiazyl radical or a triazolyl radical, an isoxazolyl radical or a pyrazolyl radical, which may be substituted or unsubstituted;

$R^2$, $R^3$, $R^4$ are each independently $C_1$-$C_{20}$-alkyl, $C_0$-$C_{20}$-alkylene-$C_3$-$C_{18}$-cycloalkyl, $C_0$-$C_{20}$—alkyleneheterocycloalkyl having from 3 to 18 ring atoms, $C_0$-$C_{20}$-alkylene-$C_1$-$C_{20}$-alkoxy, $C_0$-$C_{20}$-alkylene-$C_6$-$C_{18}$-aryloxy, $C_0$-$C_{20}$-alkylene-$C_6$-$C_{18}$-aryl, $C_0$-$C_{20}$—alkyleneheteroaryl having from 5 to 18 ring atoms, where the aforementioned radicals may be substituted by hydroxyl, halogen, alkyl, cycloalkyl, heterocycloalkyl, aryl, heteroaryl or amino, or be unsubstituted; pseudohalogen or halogen, further preferred $R^2$, $R^3$ and $R^4$ radicals being specified above;

o is from 0 to 3, where the $R^3$ radicals, when o>1, may be the same or different;

n, p are each independently from 0 to 2, where the $R^2$ or $R^4$ radicals, when n or p>1, may be the same or different;

$X^2$ is CH or $CR^2$;

$X^3$ is CH or $CR^3$;

$X^4$ are each independently CH or $CR^4$.

In the compounds of the formula (II), $X^2$, $X^3$ and $X^4$ are most preferably each CH. In a further very particularly preferred embodiment, the indices n, o and p are each 0.

The metal atom M in the organometallic complexes of the general formula (I) is preferably a metal atom selected from the group consisting of Fe, Cu, Ni, Ru, Rh, Pd, Pt, Os, Ir, Re, Ag, Cu, Au, Hg, Cd, Nb, Zr, Ca, Cr, Mo, W, Mn, Tc, B, Al, Si, alkali metals and alkaline earth metals, preferably Ir, Co, Rh, Ni, Pd, Pt, Fe, Ru, Os, Cr, Mo, W, Mn, Tc, Re, Cu and Au, in any oxidation state possible for the corresponding metal atom. The metal atom M is more preferably selected from the group consisting of Ir, Rh, Ru, Pd and Pt, most preferably selected from the group of Ir, Pd and Pt. The metal atom M is very especially preferably Ir(III).

The R¹ radical is more preferably a radical of the formula

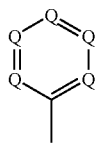

where Q is in each case independently CR$^a$ or N, where at least one Q group in the ortho-position to the bonding site is N. In general, the aforementioned R¹ radical comprises a total of 1, 2, 3 or 4 nitrogen atoms, preferably 1, 2 or 3 nitrogen atoms, more preferably 1 or 2 nitrogen atoms. The further ring members in the aforementioned R¹ radical are carbon atoms. R$^a$ is independently hydrogen, alkyl, cycloalkyl, heterocycloalkyl, aryl, heteroaryl, amino or a group having donor or acceptor action;
or a radical of the formulae

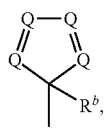 (a)

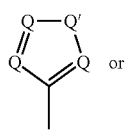 or (b)

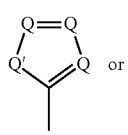 or (c)

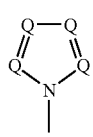 (d)

where Q is in each case independently CR$^a$ or N, where at least one Q group in the ortho-position to the bonding site is N, and Q' is CR$^a_2$, O, S or NR$^c$. In general, the aforementioned R¹ radical (a) comprises a total of 1, 2, 3 or 4 nitrogen atoms, preferably 1, 2 or 3 nitrogen atoms, more preferably 1 or 2 nitrogen atoms. The aforementioned R¹ radical (b) generally comprises a total of 1, 2, 3 or 4 nitrogen atoms, preferably 1, 2 or 3 nitrogen atoms, more preferably 1 or 2 nitrogen atoms. It is likewise possible that the R¹ radical (b) comprises a total of 1, 2 or 3 nitrogen atoms and 1 oxygen atom or 1 sulfur atom, preferably 1 or 2 nitrogen atoms and 1 oxygen atom or 1 sulfur atom, more preferably 1 nitrogen atom and 1 oxygen atom or 1 sulfur atom. The aforementioned R¹ radical (d) comprises generally a total of 1, 2, 3 or 4 nitrogen atoms, preferably 1, 2 or 3 nitrogen atoms, more preferably 1 or 2 nitrogen atoms. The further ring members in the aforementioned R¹ radicals are carbon atoms. R$^a$, R$^b$ and R$^c$ are each independently hydrogen, alkyl, cycloalkyl, heterocycloalkyl, aryl, heteroaryl, amino, CF$_3$, CN, alkoxy or F.

Examples of suitable R¹ radicals are:

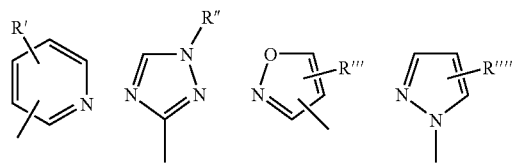

where R', R'', R''' and R'''' may each be as defined for R$^a$.

In addition, the aforementioned R¹ radicals may additionally bear fused groups, preference being given to benzofusions. One example of a suitable benzofused R¹ radical is:

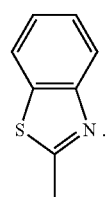

Examples of particularly preferred triphenylene derivatives of the formula II are specified below, where the triphenylene skeleton may optionally bear further substituents and/or one or more CH groups of the triphenylene base skeleton may be replaced by N:

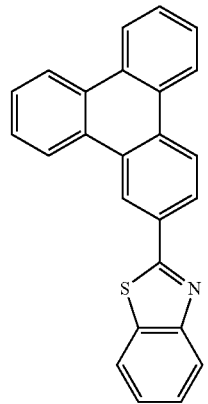

(IIa)

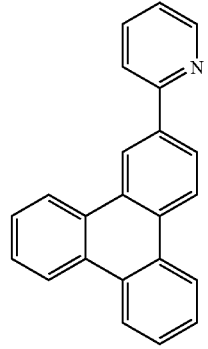

(IIb)

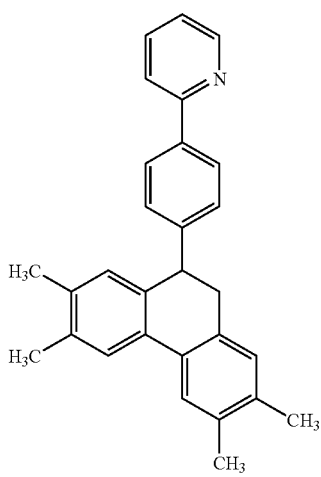
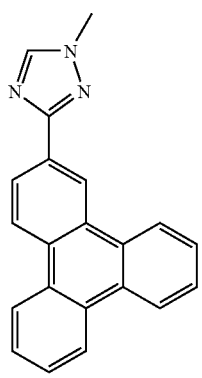
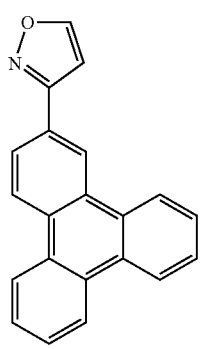
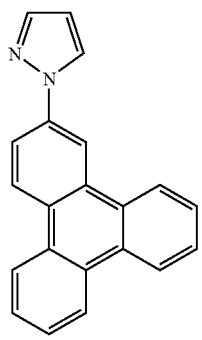

The ligand $L_1$ based on a compound of the general formula (II) may be uncharged, monoanionic or dianionic, and monodentate or bidentate. The ligand $L_1$ in the organometallic complexes of the general formula (I) is preferably a monoanionic bidentate ligand.

The organometallic complexes of the general formula (I) comprise one, two or three ligands $L_1$, where, in the case when more than one ligand $L_1$ is present in the organometallic complexes of the formula (I), the ligands $L_1$ may be the same or different. In one embodiment of the present invention, the organometallic complex of the general formula (I) comprises two ligands $L_1$. This means that q in the organometallic complexes of the general formula (I) is 1, 2 or 3, preferably 1 or 2, more preferably 2, where the ligands $L_1$, when q>1, may be the same or different.

The ligand $L_2$ in the organometallic complexes of the general formula (I) is a monoanionic or dianionic ligand which may be monodentate or bidentate.

Suitable monoanionic or dianionic ligands $L_2$, which may be monodentate or bidentate, are ligands used customarily as monodentate or bidentate, monoanionic or dianionic ligands.

Suitable monoanionic monodentate ligands are, for example, halides, especially $Cl^-$ and $Br^-$, pseudohalides, especially $CN^-$, cyclopentadienyl ($Cp^-$), hydride, alkyl radicals which are bonded to the metal M via a sigma bond, for example $CH_3$, alkylaryl radicals which are bonded to the metal M via a sigma bond, for example benzyl.

Suitable monoanionic bidentate ligands are, for example, acetylacetonate and derivatives thereof, picolinate, Schiff bases, amino acids, arylacyl, for example phenylpyridine, and the further bidentate monoanionic ligands specified in WO 02/15645, preference being given to acetylacetonate and picolinate.

Suitable dianionic bidentate ligands are, for example, dialkoxides, dicarbonates, dicarboxylates, diamides, diimides, dithiolates, biscyclopentadienyls, bisphosphonates, bissulfonates and 3-phenylpyrazole.

Particularly preferred suitable ligands $L_2$ are the following ligands (a) to (f)

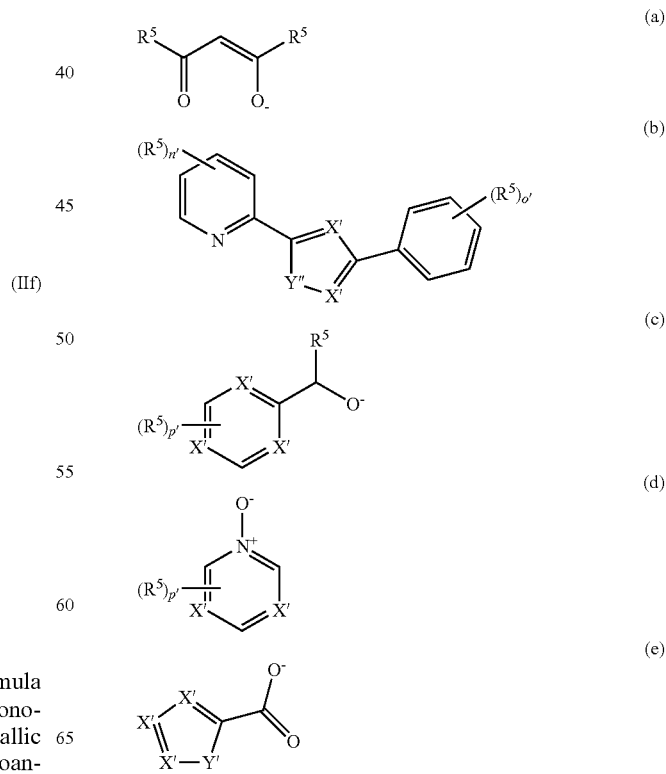

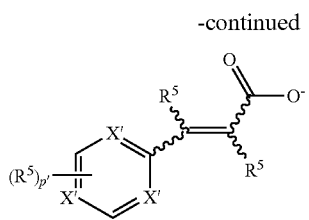

in which
R⁵ in each of the ligands (a) to (f) is independently hydrogen, $C_1$-$C_{20}$-alkyl, $C_0$-$C_{20}$-alkylene-$C_3$-$C_{18}$-cycloalkyl, $C_0$-$C_{20'}$-alkyleneheterocycloalkyl having from 3 to 18 ring atoms, $C_0$-$C_{20}$-alkylene-$C_1$-$C_{20}$-alkoxy, $C_0$-$C_{20}$-alkylene-$C_6$-$C_{18}$-aryloxy, $C_0$-$C_{20}$-alkylene-$C_6$-$C_{18}$-aryl, $C_0$-$C_{20}$-alkyleneheteroaryl having from 5 to 18 ring atoms, where the aforementioned radicals may each be substituted by hydroxyl, halogen, pseudohalogen, alkyl, cycloalkyl, heterocycloalkyl, aryl, heteroaryl, amino, —C(O)R', —C(O)OR", —OC(O)R'", —OC(O)OR"", where R', R", R'" and R"" are each independently hydrogen, alkyl, cycloalkyl, heterocycloalkyl, aryl, heteroaryl or amino, or be unsubstituted; hydroxyl, halogen, pseudohalogen, phosphonate, phosphate, phosphine, phosphine oxide, phosphoryl, sulfonyl, sulfonate, sulfate, sulfone, amino, polyether, silyl-$C_1$-$C_{20}$-alkyl, silyl-$C_0$-$C_{20}$—alkylene-$C_6$-$C_{18}$-aryl, silyl-$C_0$-$C_{20}$-alkylene-$C_1$-$C_{20}$-alkoxy, —C(O)R', —C(O)OR", —OC(O)R'", —OC(O)OR"", where R', R", R'" and R"" are each independently hydrogen, alkyl, cycloalkyl, heterocycloalkyl, aryl, heteroaryl or amino;

R⁵ is preferably hydrogen, $C_1$-$C_8$-alkyl, $C_0$-$C_4$-alkylene-$C_3$-$C_8$-cycloalkyl, $C_0$-$C_4$-alkylene-$C_6$-$C_{18}$-aryl;

X' are each independently $CR^5$ or N;

Y' is $C(R^5)_2$, $NR^S$, O or S;

Y'" is $N^-$;

n' is 1, 2, 3 or 4;

o' is 1, 2, 3, 4 or 5, p' is 1 or 2.

The ligand $L_2$ is most preferably selected from the group consisting of β-diketonates such as acetylacetonate and derivatives thereof, picolinate, amino acid anions and monoanionic bidentate ligands of the general formula (b), where all X' groups in the formula (b) are more preferably N.

The wavy line in the ligands of the general formula (f) means that all possible cis/trans isomers are encompassed by the general formula (f).

The inventive organometallic complexes of the formula (I) may have 0, 1, 2, 3 or 4 ligands $L_2$. In the presence of more than one ligand $L_2$ in the organometallic complexes of the formula (I), the ligands $L_2$ may be the same or different. The organometallic complexes of the general formula (I) preferably have one or two ligands $L_2$. This means that r in the organometallic complexes of the formula (I) is from 0 to 4, preferably 1 or 2.

The organometallic complexes of the formula (I) may additionally optionally have one or more uncharged mono- or bidentate ligands $L_3$.

Suitable uncharged monodentate or bidentate ligands $L_3$ are preferably selected from the group consisting of phosphines, both monophosphines and bisphosphines; phosphonates, both monophosphonates and bisphosphonates, and derivatives thereof; arsenates, both monoarsenates and bisarsenates, and derivatives thereof; phosphites, both monophosphites and bisphosphites; CO; pyridines, both monopyridines and bispyridines; nitriles, dinitriles, allyl, diimines, unconjugated dienes and conjugated dienes which form a π-complex with the metal M. Particularly preferred uncharged monodentate or bidentate ligands $L_3$ are selected from the group consisting of phosphines, both monophosphines and bisphosphines, preferably trialkyl-, triaryl- or alkylarylphosphines, more preferably $PAr_3$, where Ar is a substituted or unsubstituted aryl radical and the three aryl radicals in $PAr_3$ may be the same or different, more preferably $PPh_3$, $PEt_3$, $PnBu_3$, $PEt_2Ph$, $PMe_2Ph$, $PnBu_2Ph$; phosphonates and derivatives thereof, arsenates and derivatives thereof, phosphites, CO; pyridines, both monopyridines and bispyridines, where the pyridines may be substituted by alkyl or aryl groups; nitriles and dienes which form a π-complex with the metal M, preferably $η^4$-1,4-dibenzyl-1,3-butadiene, $η^4$-2,4-hexadiene, $η^4$-3-methyl-1,3-pentadiene, $η^4$-1,4-dibutyl-1,3-butadiene, $η^4$-1,4-bis(trimethylsilyl)-1,3-butadiene and $η^2$ or $η^4$-cyclooctadiene (in each case 1,3 and 1,5), more preferably 1,4-diphenyl-1,3-butadiene, 1-phenyl-1,3-pentadiene, 2,4-hexadiene, butadiene, $η^2$-cyclooctene, $η^4$-1,3-cyclooctadiene and $η^4$-1,5-cyclooctadiene. Very particularly preferred uncharged monodentate ligands are selected from the group consisting of $PPh_3$, $P(OPh)_3$, CO; pyridine, nitriles and derivatives thereof. Suitable uncharged monodentate or bidentate ligands are preferably 1,4-diphenyl-1,3-butadiene, 1-phenyl-1,3-pentadiene, 2,4-hexadiene, $η^4$-cyclooctadiene and $η^2$-cyclooctadiene (in each case 1,3 and 1,5).

The organometallic complexes of the formula (I) may have 0, 1, 2, 3 or 4 uncharged monodentate or bidentate ligands $L_3$. If more than 1 ligand $L_3$ is present in the transition metal complexes of the formula (I), the ligands $L_3$ may be the same or different. In a preferred embodiment, the organometallic complex of the general formula (I) comprises 0 ligands $L_3$. This means that s in the organometallic complexes of the general formula (I) is from 0 to 4, preferably 0.

In a particularly preferred embodiment, the present invention relates to organometallic complexes of the formula (I), in which M is Ir(III);

$L_2$ is a monoanionic bidentate ligand, preferred monoanionic bidentate ligands having already been specified above, q is 1 or 2, preferably 2;

r is 1 or 2;

s is 0;

$L_1$ is a monoanionic bidentate ligand derived from a triphenylene derivative of the formula (IIa), preferred triphenylene derivatives having been specified above, where the sum of q+r=3.

Particularly preferred organometallic complexes of the formula (I) are organometallic complexes of the following formulae (Ia), (Ib) and (Ic) and (Id), (Ie) and (If)

(Ia)

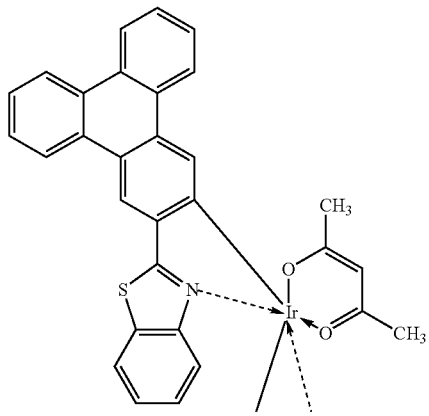

(Ib)

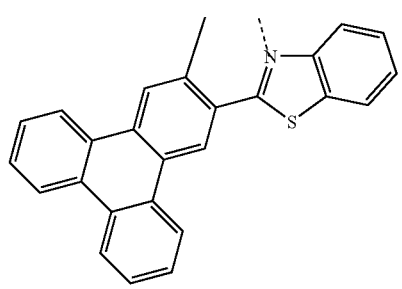

(Ic)

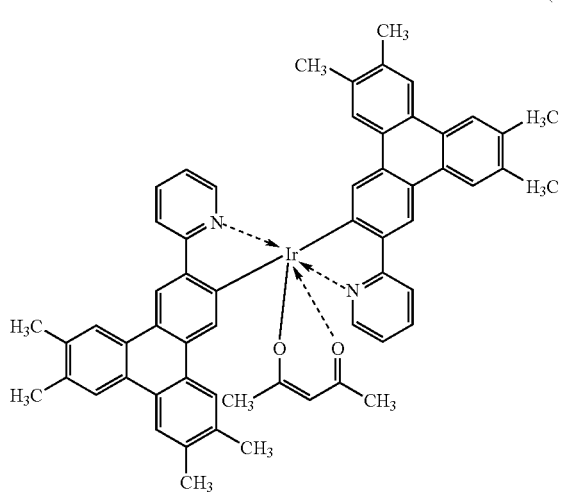

(Id)

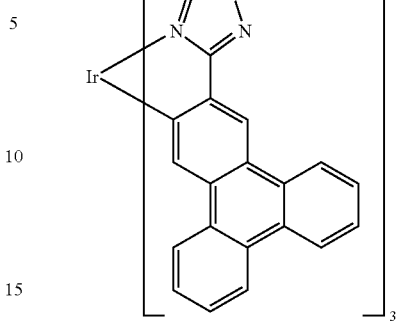

The inventive organometallic complexes (I) can be prepared by all processes known to those skilled in the art.

In a preferred embodiment, the preparation is effected by
(a) reacting metal salts or metal complexes which comprise the desired metal M and optionally comprise one or more ligands $L_3$ with a first ligand $L_1$ or $L_2$ to give metal complexes which bear either one or more ligands $L_1$ or one or more ligands $L_2$, if appropriate in addition to one or more ligands $L_3$;
(b) reacting the metal complexes obtained in step (a) with a second ligand $L_1$ when the metal complex obtained in step (a) comprises one or more ligands $L_2$, or with one ligand $L_2$ when the metal complex obtained in step (a) comprises one or more ligands $L_1$, to obtain an organometallic complex of the formula (I), step (b) being dispensed with in the case that the organometallic complex of the formula (I) does not comprise any ligand $L_2$, i.e. when r in the organometallic complex of the formula (I) is 0.

The reaction conditions for the preparation of organometallic complexes proceeding from suitable ligands are known to those skilled in the art.

The inventive organometallic complexes of the formula (I) are suitable as emitter materials especially for use in OLEDs. In general, the emitter materials are used together with one or more suitable matrix materials. One advantage of the inventive transition metal complexes is that, owing to their structure, they can be used in high concentrations in OLEDs, especially in the light-emitting layer, without formation of dimers and hence quenching of luminescence occurring. As a result, it is possible to provide OLEDs with high luminescence efficiency and high lifetime of the light-emitting layer.

Typically, one or more organometallic complexes of the formula (I) are present in the light-emitting layer of an OLED, preferably together with one or more matrix materials. The concentration of the organometallic complexes of the formula (I) in the matrix materials is generally from >0 to ≦100% by weight, preferably from ≧5 to ≦50% by weight, more preferably from ≧10 to ≦30% by weight and most preferably from ≧11 to ≦25% by weight, based on the light-emitting layer. The matrix material or the matrix materials are correspondingly present preferably in a concentration of from 0 to <100% by weight, preferably from ≧50 to ≦95% by weight, more preferably from ≧70 to ≦90% by weight, most preferably from 75 to ≦89% by weight.

Suitable matrix materials are known to those skilled in the art. Examples of suitable matrix materials are published, for example, in Organic Light-Emitting Materials and Devices (Optical Science and Engineering Series), Ed.: Z. Li, H. Meng, CRC Press Inc., 2006.

The present application further provides for the use of the inventive organometallic complexes of the formula (I) or of the inventive mixtures comprising at least one organometallic complex of the formula (I) in organic light-emitting diodes. Preference is given to using the organometallic complexes of the formula (I) in the light-emitting layer of organic light-emitting diodes.

The present invention further provides for the use of the inventive organometallic complexes of the formula (I) as emitter materials.

OLEDs and the construction of suitable OLEDs are known to those skilled in the art.

The present invention further provides a triphenylene derivative of the general formula (IIa)

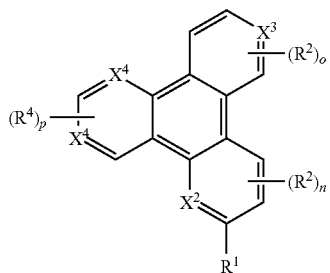

(IIa)

in which:

$R^1$ is an N-comprising radical, preferably a heterocyclic radical which may be substituted or unsubstituted, more preferably an N-heterocyclic radical comprising at least one nitrogen atom, most preferably a mono-, bi- or tricyclic heteroaromatic radical which has at least one nitrogen atom and may be substituted or unsubstituted, very especially preferably a pyridyl or benzothiazyl radical or a triazolyl radical, an isoxazolyl radical or a pyrazolyl radical, which may be substituted or unsubstituted;

$R^2$, $R^3$, $R^4$ are each independently $C_1$-$C_{20}$-alkyl, $C_0$-$C_{20}$-alkylene-$C_3$-$C_{18}$-cycloalkyl, $C_0$-$C_{20}$-alkyleneheterocycloalkyl having from 3 to 18 ring atoms, $C_0$-$C_{20}$-alkylene-$C_1$-$C_{20}$-alkoxy, $C_0$-$C_{20}$-alkylene-$C_6$-$C_{18}$-aryloxy, $C_0$-$C_{20}$-alkylene-$C_6$-$C_{18}$-aryl, $C_0$-$C_{20}$-alkyleneheteroaryl having from 5 to 18 ring atoms, where the aforementioned radicals may be substituted by hydroxyl, halogen, pseudohalogen, alkyl, cycloalkyl, heterocycloalkyl, aryl, heteroaryl, amino, —C(O)R', —C(O)OR'', —OC(O)R''', —OC(O)OR'''', where R', R'', R''' and R'''' are each independently hydrogen, alkyl, cycloalkyl, heterocycloalkyl, aryl, heteroaryl or amino, or be unsubstituted; hydroxyl, halogen, pseudohalogen, phosphonate, phosphate, phosphine, phosphine oxide, phosphoryl, sulfonyl, sulfonate, sulfate, amino, polyether, silyl-$C_1$-$C_{20}$-alkyl, silyl-$C_0$-$C_{20}$-alkylene-$C_6$-$C_{18}$-aryl, silyl-$C_0$-$C_{20}$-alkylene-$C_1$-$C_{20}$-alkoxy, —C(O)R', —C(O)OR'', —OC(O)R''', —OC(O)OR'''', where R', R'', R''' and R'''' are each independently hydrogen, alkyl, cycloalkyl, heterocycloalkyl, aryl, heteroaryl or amino;

o is from 0 to 3, where the $R^3$ radicals, where o>1, may be the same or different;

n, p are each independently from 0 to 2, where the $R^2$ or $R^4$ radicals, when n or p>1, may be the same or different;

$X^2$ is N, CH or $CR^2$;
$X^3$ is N, CH or $CR^3$;
$X^4$ are each independently N, CH or $CR^4$.

Preferred embodiments of the definitions of the radicals and indices $R^1$, $R^2$, $R^3$, $R^4$, n, o, p, $X^2$, $X^3$ and $X^4$ are specified above.

The inventive triphenylene derivatives may be prepared by a process comprising the steps of:

(i) preparing an arylboronic acid or an arylboronic acid derivative (V) by reaction, for example catalyzed reaction, for which, for example, a Pd-comprising catalyst can be used, of an aromatic compound of the formula IV which has been functionalized with a Y group with a corresponding boron compound:

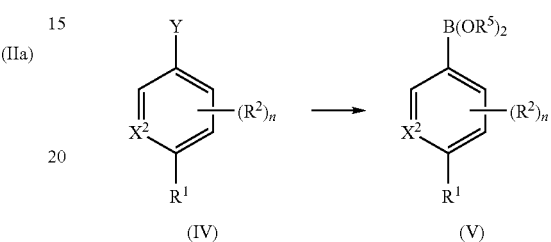

in which

Y is halogen and $R^5$ is H, $C_1$-$C_6$-alkyl, or two $R^5$ radicals form a diatomic bridge between the oxygen atoms, where the atoms of the bridge may be substituted or unsubstituted;

(ii) palladium-catalyzed reaction of one equivalent of the arylboronic acid or of the arylboronic acid derivative of the formula V with a biphenyl derivative of the formula VI which has been functionalized with two z groups to obtain a compound of the formula VII

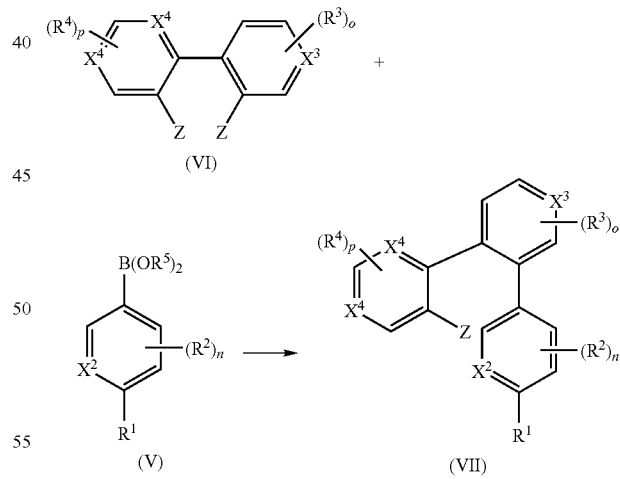

in which z is halogen or OTf;

(iii) palladium-catalyzed intramolecular cyclization of the compound of the formula VII to obtain the desired triphenylene derivatives of the formula IIb.

A preferred process for preparing inventive triphenylene derivatives in which $R^1$ is a 2-pyridyl radical is shown by way of example hereinafter.

Scheme 1
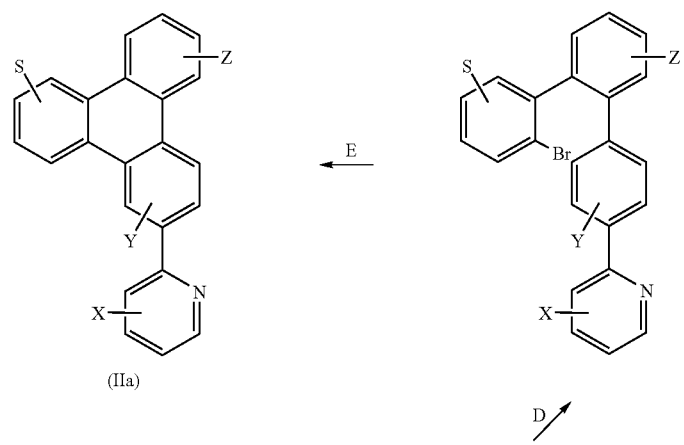
(IIa)
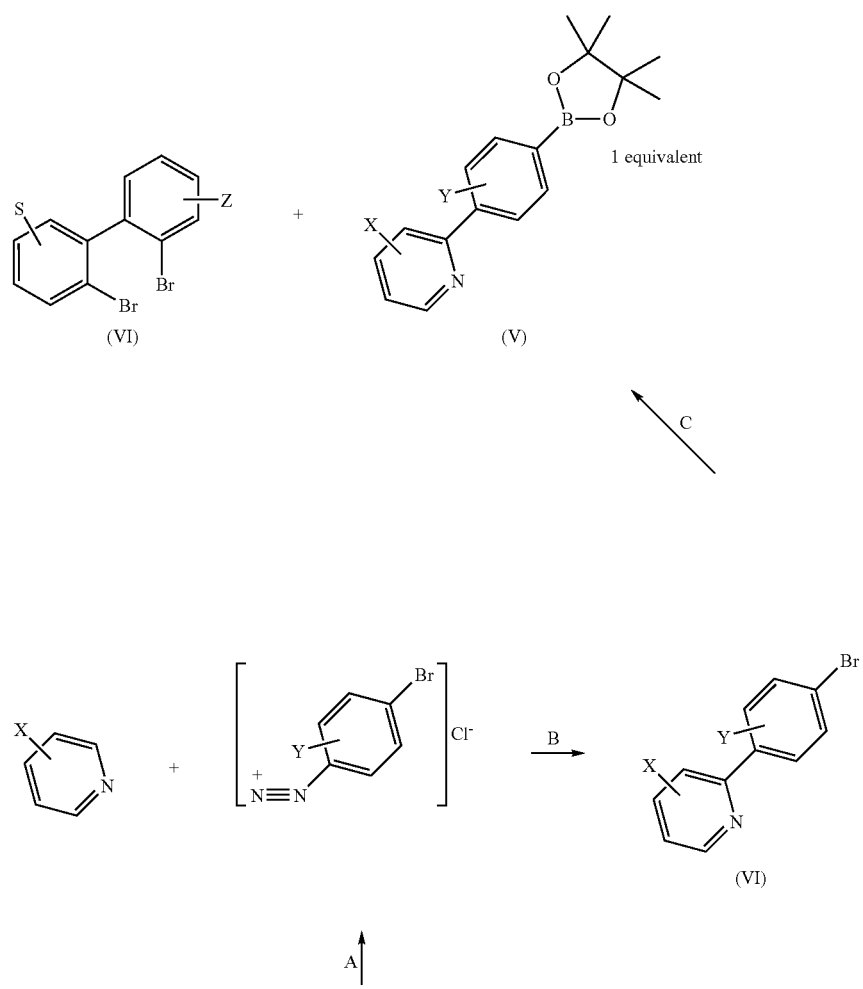

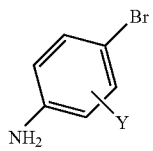

X, Y, Z and S each represent one or more substituents, suitable substituents Y, Z and S corresponding to the substituents $(R^2)_n$, $(R^3)_o$ and $(R^4)_p$, which are each defined above. The X group corresponds to the substituents of the $R^1$ radical, preferred substituents being $R^a$ and $R^b$ which are defined above. Suitable substituents X, Y, Z and S are, for example, Me, tBu, $CF_3$, F and OMe.

In steps A, B and C in Scheme 1, a suitable arylboronic acid or a suitable arylboronic acid derivative (V) is prepared. First, an aromatic compound of the formula (IV) functionalized with a Y group (in the present case Br) is prepared. In the present scheme, in which $R^1$ is pyridine, the compound of the formula (IV) is prepared by azo coupling of the corresponding aryl group functionalized with halogen (in the present case Br) with pyridine. The resulting compound of the formula (IV) (in the present scheme 2-(4-bromophenyl)pyridine) is converted, preferably by palladium-catalyzed reaction, to the corresponding arylboronic acid or the corresponding arylboronic acid derivative (V). Suitable reactions are known to those skilled in the art. In the present scheme, 2-(4-bromophenyl)pyridine is reacted with bis(pinacolato)diboron in the presence of $Pd(dba)_3$ and tricyclohexylphosphine in catalytic amounts in the presence of a base, KOAc.

The resulting arylboronic acid or the resulting arylboronic acid derivative of the formula (V) is reacted in step D (step (ii) of the process according to the invention) with a biphenyl derivative of the formula (VI) functionalized with two z groups. The z groups are halogen or OTf, in the present case in Scheme 1 Br. The reaction is effected under palladium catalysis. The palladium catalyst used in step D in the present Scheme 1 is preferably $Pd(PPh)_4$ in the presence of a base, $Na_2CO_3$.

To prepare the desired triphenylene derivative of the formula (IIa), a palladium-catalyzed intramolecular cyclization is effected in step E in Scheme 1 (step (iii) of the process according to the invention). The palladium catalyst used in the present Scheme 1 is $Pd(OAc)_2$ in catalytic amounts in the presence of a base, $K_2CO_3$.

The palladium-catalyzed intramolecular cyclization for preparing the desired triphenylene derivatives of the formula (IIa) which has been performed in step (iii) was to date unknown in the prior art. It has been found that the direct synthesis of fused aromatic systems (triphenylene derivatives) is possible in this way.

A further route to the preparation of the inventive triphenylene derivatives of the formula (IIa) is possible proceeding from 2-triphenylenecarboxylic acids, as shown in the general Scheme 2:

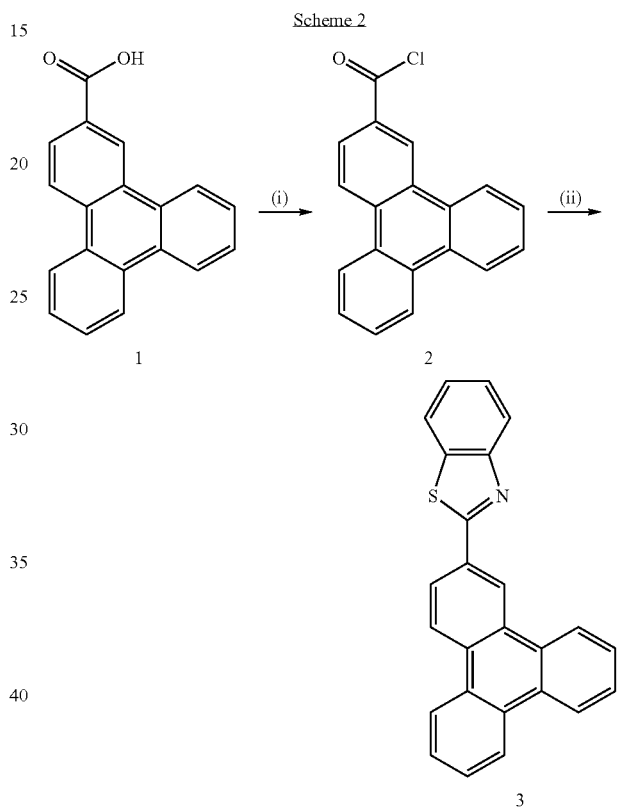

Scheme 2

In step (i), 2-triphenylenecarboxylic acid is converted by processes known to those skilled in the art to the corresponding acid chloride. The reaction can be effected with any chlorinating agent known to those skilled in the art, for example with thionyl chloride.

Subsequently, in step (ii), the resulting acid chloride is reacted, for example, with o-aminothiophenol to obtain an inventive triphenylene derivative of the formula (IIa).

Scheme 2 is merely by way of example. The triphenylene skeleton may bear further substituents or some of the carbon atoms present in the triphenylene skeleton may be replaced by nitrogen atoms.

The triphenylenecarboxylic acids used may be prepared by processes known to those skilled in the art.

A further route to the preparation of the inventive triphenylene derivatives via 2-triphenylenecarboxylic acid is shown in scheme 3. Scheme 3 shows, by way of example, a process for preparing inventive triphenylene derivatives of the formulae (Id) and (Ie). A route to the preparation of 2-triphenylenecarboxylic acid is likewise shown in scheme 3:

Scheme 3

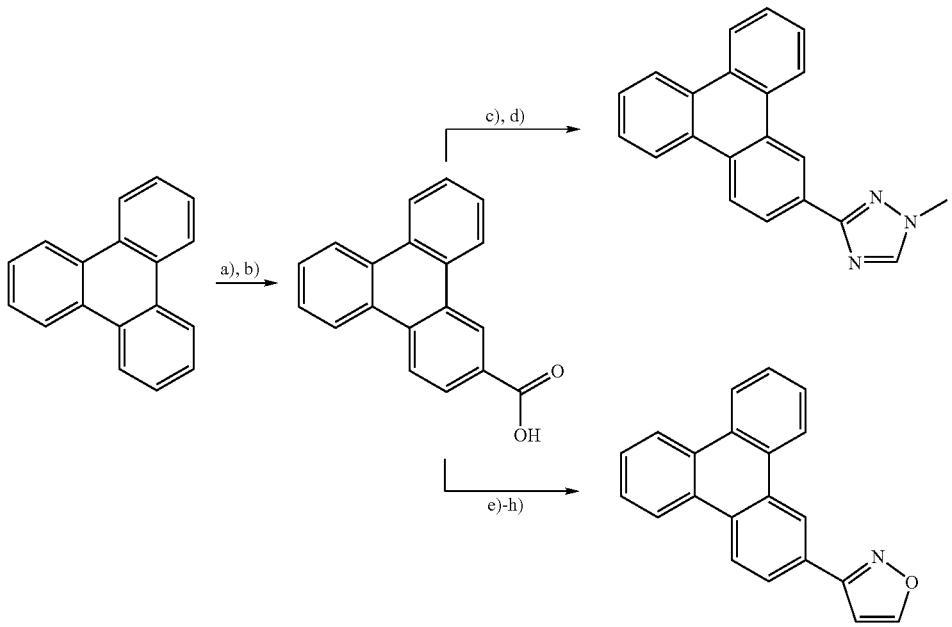

Suitable reaction conditions can be taken from analogous reactions in the literature. Suitable literature with regard to the individual steps specified in scheme 3 is listed below. Particularly preferred reaction conditions are specified in the example part which follows.

a) and b) analogous to publication for dihydropyrene: D. M. Connor, S. D. Scott, D. M. Collard, Chr. L. Liotta, D. A. Schiraldi, *J. Org. Chem.* 1999, 64, 6888-6890.

c) Analogous to publication via 3-methyl-4-nitrobenzoic acid: D. J. Sall, A. E. Arfesten, J. A. Bastian, M. L. Denney, C. S. Harms, *J. Med. Chem.*, 1997, 40, 2843-2857.

d) Analogous to publication via 3-(1-methyl-1,2,4-triazol-3-yl)azabicyclo[2.2.2]octane: H. J. Wadsworth, S. M. Jenkins, B. S. Orlek, F. Cassidy, M. S. G. Clark, F. Brown, G. J. Riley, D. Graves, J. Hawkins, Chr. B. Naylor, *J. Med. Chem.* 1992, 35, 1280-1290.

e) and f) analogous to publication for iodobenzoic acid: S. E. Gibson et al., *Chem. Eur. J.* 2005, 11, 69-80.

g) Analogous to publication for benzaldehyde oxime: P. Aschwanden et al. *Org. Lett.* 2005, 7, 5741-5742.

h) Analogous to publication for 3-substituted isoxazoles: A. Baranski, *Pol. J. Chem.* 1982, 56, 1585-1589 and R. G. Micetich, *Can. J. Chem.* 1970, 48, 467-476 and S.-R. Sheng, X.-L. Liu, Q. Xu, C.-S. Song, *Synthesis* 2006, 14, 2293-2296.

Scheme 3 is merely by way of example. The triphenylene skeleton may bear further substituents or some of the carbon atoms present in the triphenylene skeleton may be replaced by nitrogen atoms.

A further route to the preparation of the inventive triphenylene derivatives proceeding from a triphenylene skeleton may proceed via a bromination of triphenylene analogously to processes known to those skilled in the art. Scheme 4 shows this route by way of example for the preparation of the triphenylene derivative of the formula (If):

Scheme 4

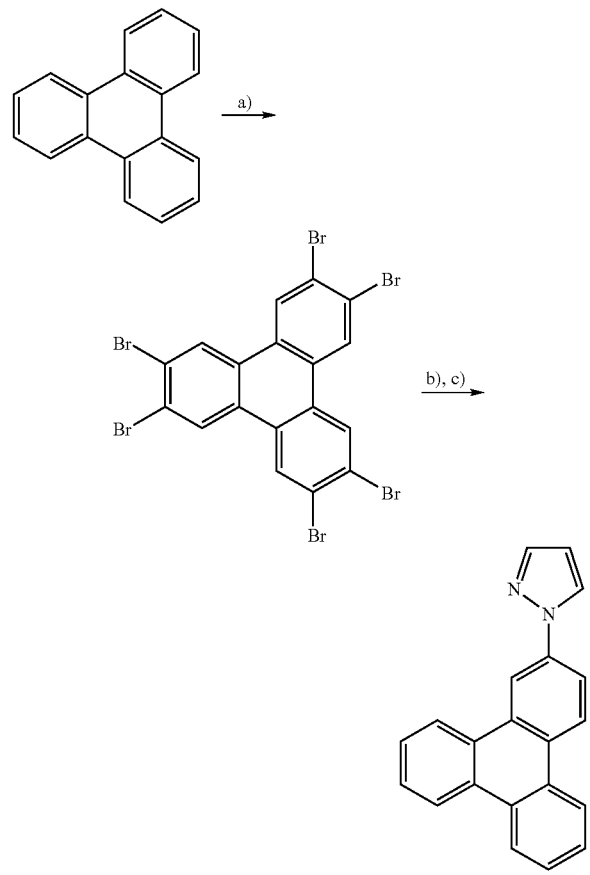

Suitable reaction conditions can be taken from analogous reactions in the literature. Suitable literature with regard to the individual steps specified in scheme 4 is listed below. Particularly preferred reaction conditions are specified in the example part which follows.

a) Analogous to publication by R. Breslow, Ronald B. Juan, Bernhard R. Q. Kluttz, C.-z. Xia, *Tetrahedron* 1982, 38, 863-867.

b) Analogous to publication for phenylpyrazole: J. C. Antilla, J. M. Baskin, T. E. Barder, S. L. Buchwald, *J. Org. Chem.* 2004, 69, 5578-5587.

$c_1$) Analogous to publication for dibromochlorobenzene: K. Menzel, L. Dimichele, P. Mills, D. E. Frantz, T. D. Nelson, M. H. Kress, *Syn. Lett.* 2006, 12, 1948-1952.

$c_2$) Analogous to publication for tetrabromoaromatics: G. Dorman, J. D. Olszewski, G. D. Prestwich, Y. Hong, D. G. Ahem, David G. *J. Org. Chem.* 1995, 60, 2292-2297.

$c_3$) Analogous to publication for debromination of aromatics: S. Arai, M. Oku, T. Ishida, T. Shioiri; *Tetrahedron Lett.* 1999, 40, 6785-6790.

Scheme 4 is merely by way of example. The triphenylene skeleton may bear further substituents or some of the carbon atoms present in the triphenylene skeleton may be replaced by nitrogen atoms. In particular, it is also possible to prepare the corresponding inventive triphenylene derivatives of the formulae (Id) and (Ie) according to scheme 4.

In addition, the inventive triphenylene derivatives can be obtained by aryne coupling. A general scheme 5 is specified below. Scheme 5a shows the preparation by aryne coupling using the example of the preparation of the compounds of the formulae (Id), (Ie) and (If):

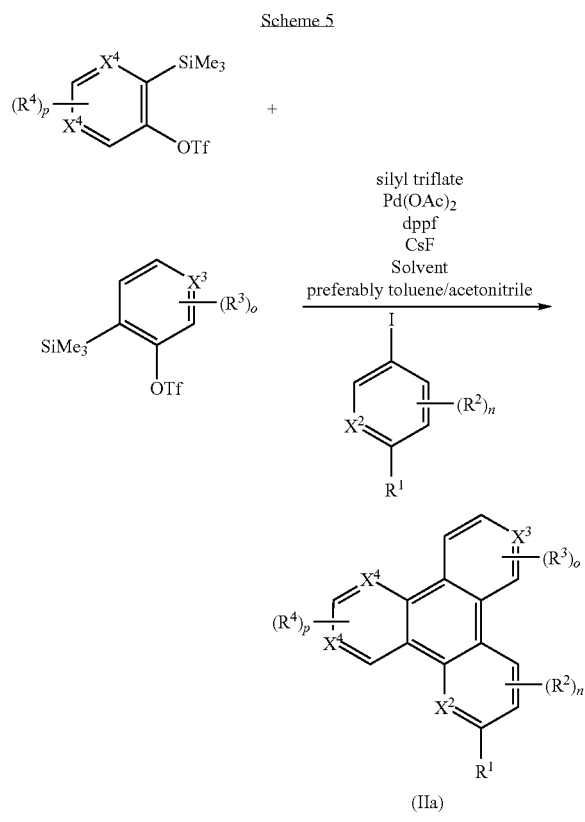

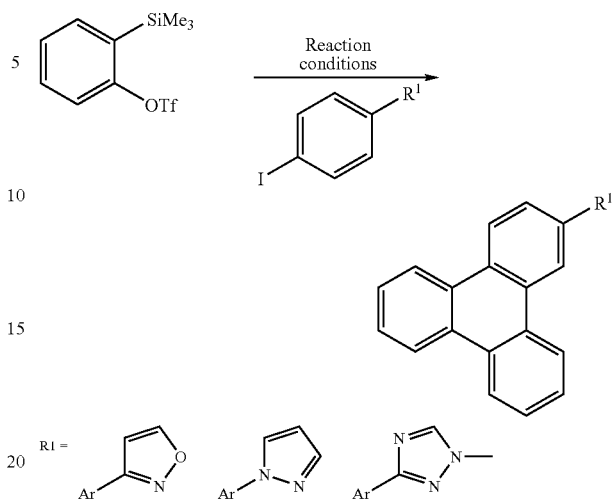

The reaction conditions are analogous to the preparation of methyltriphenylene, as disclosed, for example, in Z. Liu, R. Larock, *J. Org. Chem.* 2007, 72, 223-232. Particularly preferred reaction conditions are specified in the example part which follows.

The examples which follow provide additional illustration of the invention.

EXAMPLES

Preparation of Triphenylene Derivatives of the Formula (IIa) According to Scheme 1

1. Preparation of 2-(4-(4,4,5,5-tetramethyl-1,3,2-dioxaborolane)pyridine 0.39 g (0.4 mmol) of Pd(dba)$_3$ and 0.28 g (1 mmol) of tricyclohexylphosphine are suspended in 10 ml of dry dioxane under a nitrogen atmosphere. The resulting mixture is stirred at room temperature for 30 minutes. Subsequently, 5.3 g (15 mmol) of bis(pinacolato)diboron, 2.1 g (21 mmol) of KOAc and 3.3 g (14 mmol) of 2-(4-bromophenyl)pyridine are added gradually. The reaction mixture is boiled under reflux for 20 hours, cooled and treated with 10 ml of water at room temperature. The product is extracted with dichloromethane. The solvent is removed under reduced pressure and the resulting crude product is purified by means of a short silica gel column. After purification by means of the silica gel column (dichloromethane/hexane, 3:1), 82% of the desired product is obtained.

$^1$H NMR(CDCl$_3$): δ=1.37 (s, 12H), 7.22-7.26 (m, 1H), 7.72-7.80 (m, 2H), 7.92 (J=8.4 Hz, 2H), 8.02 (J=8.2 Hz, 2H), 8.71 (J=4.9 Hz, 1H).

2. Preparation of a Diphenyl Derivative of the Formula (VI) Substituted by Two Br Radicals The preparation of substituted dibromides proceeds from o-dibromobenzenes. A typical process comprises the reaction sequence of lithiation/coupling. A general process is disclosed in the following reference: H. S. M. Kabir et al., J. Chem. Soc., Perkin Trans. 1, 2001, 159-165 (synthesis of 2,2'-dibromo-4,4',5, 5'-tetramethylbiphenyl).

3. Coupling of the Arylboronic Acid Derivative (V) with the Biphenyl Derivative of the Formula (VI) Functionalized with Two Br Radicals 6.4 mmol of the dibromide (VI) and 6.4 mmol of the arylboronic acid derivative (V) (2-(4-(4,4,5,5-tetramethyl-1,3,2-dioxaborolane)pyridine) are dissolved in 25 ml of toluene. 0.4 mmol of Pd(PPh$_3$)$_4$ and 10 ml of a 4N solution of Na$_2$CO$_3$ are added, and the mixture is heated up to reflux under nitrogen. The reaction mixture is heated under reflux for 6 hours and cooled, the phases formed are separated, and the water phase is extracted with dichloromethane and dried. The solvent is removed under reduced pressure and the crude product is purified by means of a short silica gel column. After purification by column chromatography (dichloromethane/hexane, 2:1), the desired o-terphenyl derivative is obtained in from 40 to 50% yield.

4. Intramolecular Cyclization to the Triphenylene Derivative of the Formula (IIa)

2.87 mmol of the o-terphenyl derivative, 0.14 mmol of Pd(OAc)$_2$ and 5.7 mmol of K$_2$CO$_3$ are heated in 7 ml of DMA at 135° C. for 24 hours under a nitrogen atmosphere. The reaction mixture is cooled, treated with 5 ml of water and extracted with dichloromethane. The organic phase is dried, the solvent is removed under reduced pressure and the residue is purified by means of a short silica gel column (dichloromethane). After column chromatography (dichloromethane/hexane, 2:1), the desired triphenylene derivative (IIa) is obtained in from 35 to 40% yield.

5. Preparation of the Inventive Triphenylene Derivatives of the Formula (IIa) According to Scheme 2

0.8 g (2.9 mmol) of 2-triphenylenecarboxylic acid (prepared by processes known to those skilled in the art) is suspended in 15 ml of chloroform. Subsequently, 4 ml of thionyl chloride are added, and the reaction mixture is brought to reflux under a nitrogen atmosphere. After stirring under reflux for 3 hours, the clear solution is evacuated under reduced pressure and the solid residue is recrystallized from hexane/chloroform (10/1). The resulting acid chloride 2 is dissolved in 10 ml of dry 1-methylpyrrolidinone, and 0.32 ml (2.9 mmol) of o-aminothiophenol is added. The reaction mixture is stirred at 100° C. for three hours. After cooling, the solution is added to cold water and the mixture is adjusted to a pH of from 8 to 9 with 7 N aqueous ammonia. The precipitate formed is filtered, washed with water and purified by means of a short silica gel column (dichloromethane) to obtain 0.82 g (78%) of the desired triphenylene derivative (IIa) 3.

m.p.: 230 to 231° C.

6. Preparation of an Inventive Transition Metal Complex

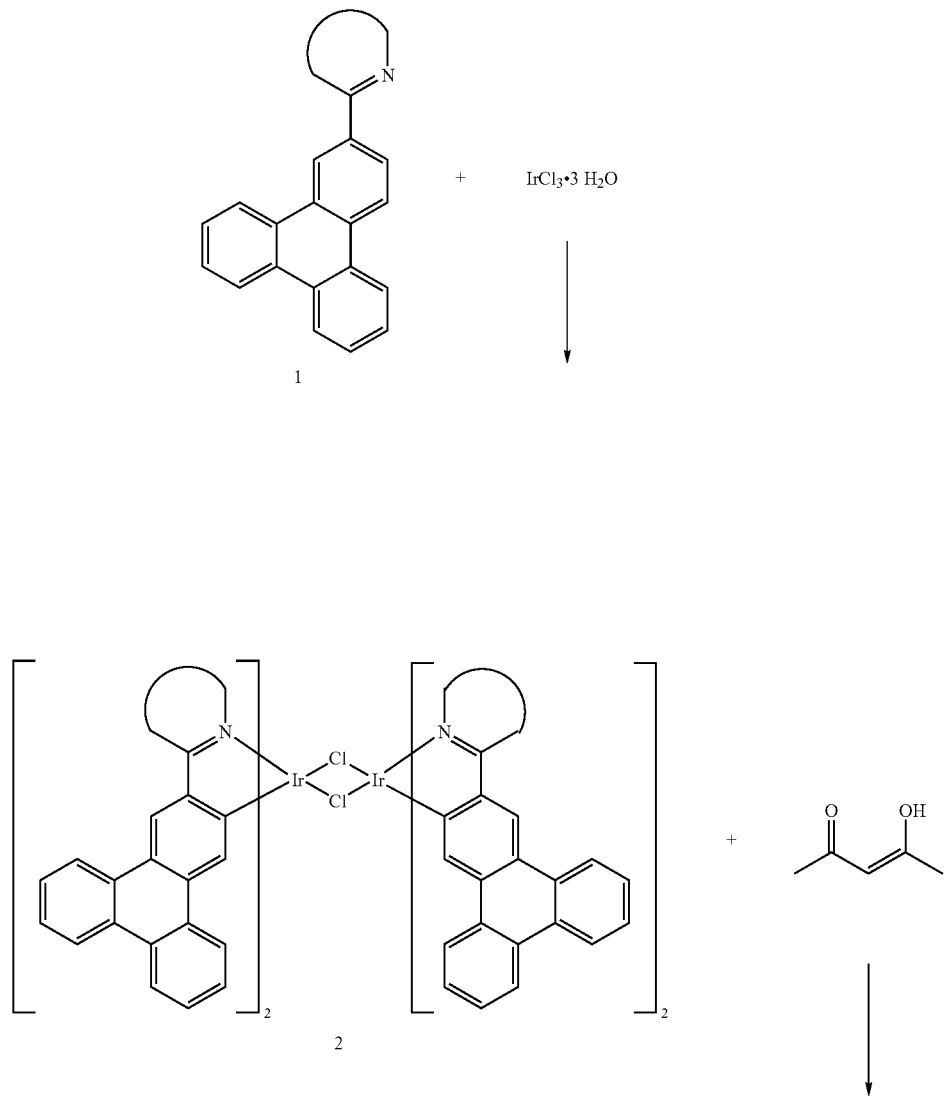

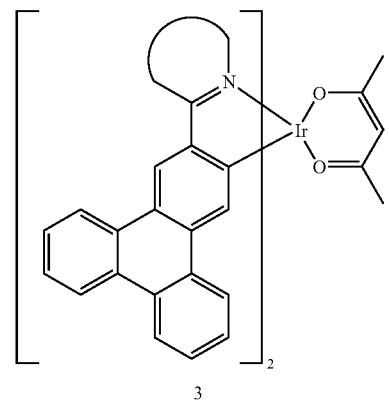

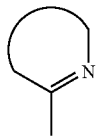

is a heterocyclic R¹ radical, suitable heterocyclic R¹ radicals being specified above General Method 0.83 mmol of the ligand 1 is suspended in 30 ml of 2-ethoxyethanol in a nitrogen atmosphere while heating. 0.38 mmol of IrCl$_3$.3H$_2$O is added and the resulting suspension is brought to reflux. Within 30 minutes, a colored precipitate appears. The reaction mixture is kept under reflux for 24 hours and then cooled to room temperature. The precipitate is collected by sedimentation in a centrifuge and washed intensively with methanol (6×15 ml). After drying under high vacuum while heating (T=80° C.), the dichloro-bridged dimer 2 is obtained in from 80 to 90% yield. These complexes are sparingly soluble in customary organic solvents and are used further without further purification.

0.16 mmol of the dichloro-bridged dimer 2 is suspended in 10 ml of 2-ethoxyethanol under a nitrogen atmosphere. 0.4 mmol of acetylacetone and from 85 to 90 mg of Na$_2$CO$_3$ are added and the reaction mixture is stirred at 100° C. for five hours. The resulting suspension is cooled to room temperature and diluted with water, and the colored precipitate is collected by sedimentation in a centrifuge, washed intensively with water/methanol (4/1.6×15 ml) and dried under high vacuum while heating (T=100° C.). After purification by column chromatography, the complex 3 is obtained as a colored solid in from 70 to 80% yield.

The Ir complexes Ia and Ib are obtained by the method specified above:

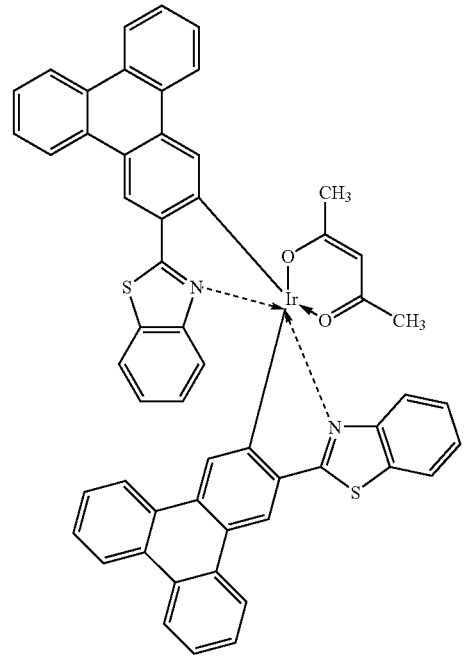

(Ia)

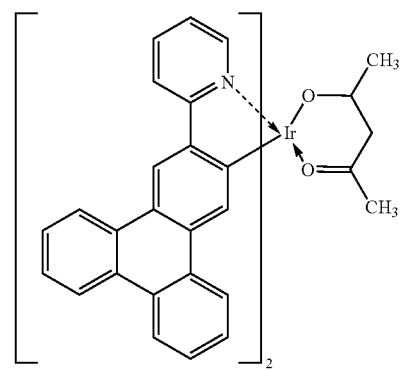

(Ib)

7. Use of the Inventive Transition Metal Complex Ia and Ib in an OLED

The diode structure is as follows:

Glass substrate comprising 120 nm of indium tin oxide

Hole injection layer (PEDOT-PSS) 200 nm

Hole transport layer composed of MTDATA, undoped; 100 nm

Emission layer composed of alpha-NPD, comprising 9% (by weight) of iridium complex Ia (Example 1) or Ib (Example 2) doped; 250 nm Layer for hole blocking and for electron transport, TPBI, 100 nm Electron injection layer (lithium fluoride) 450 nm Cathode composed of aluminum, 70 nm The results are summarized in the table which follows, Ir complex Ia having been used in Example 1 and Ir complex Ib in Example 2:

| Efficiency | Example 1 | Example 2 |
|---|---|---|
| Emission maximum | 589 nm | 541 nm |
| Efficiency | 12 lm/W at 1000 nit | 32 lm/W at 1000 nit |

8. Preparation of the Inventive Triphenylene Derivatives of the Formula (IIa) According to Scheme 3

8.1 Preparation of 2-triphenylenecarboxylic acid

Step a)

Triphenylene (1 equivalent) is reacted at 0° C. with 2.1 equivalents of $AlCl_3$ and 21.0 equivalents of $CH_3COCl$ in $CH_2Cl_2$. After stirring at room temp. for 3 hours, the reaction product (acetyltriphenylene) was obtained in 97% yield, and is used in step b).

Step b)

The reaction product obtained in step a) is admixed with 2.2 equivalents of $I_2$ (based on the crude yield of acetyltriphenylene) in pyridine solvent at room temperature. Thereafter, the mixture is kept at reflux for 45 min, and then a further portion of $I_2$ (1.0 equivalent) is added. After reflux for a further hour, NaOH, EtOH and water are added and the reaction mixture is heated to reflux for 2 h. 2-triphenylenecarboxylic acid is obtained in 76% yield (based on crude yield of acetyltriphenylene, or 74% based on triphenylene).

8.2 Preparation of a Triphenylene Derivative of the Formula IId

Step c)

1 equivalent of 2-triphenylenecarboxylic acid from step b) is reacted with $PCl_5$ (2.1 equivalents) and 1.2 equivalents of p-toluenesulfonamide in xylene, while the temperature in the course of the reaction is kept at 120° C. for 17 h. At 190° C., solvents and reagents are distilled off. After cooling to 5° C., pyridine is added and the mixture is subjected to aqueous workup. The reaction product obtained in 52% yield is used in step d).

Step d)

The reaction product obtained in step c) (1 equivalent) is admixed at 0° C. with gaseous HCl in ethanol. The mixture is stirred at room temperature for a further 24 hours. The solvent is removed almost completely. Subsequently, ethanol as the solvent, 1.3 equivalents of $MeNHNH_2$ and 2.5 equivalents of $NEt_3$ are added. The mixture is stirred at room temperature for 24 hours. At 0° C., the reaction volume is reduced to a quarter, $HCO_2H$ is added and the EtOH is drawn off completely. Subsequently, after further $HCO_2H$ has been added at room temperature and the mixture has been refluxed for 2 hours, the triphenylene derivative of the formula IId is obtained.

8.3 Preparation of a Triphenylene Derivative of the Formula IIe

Step e)

1 equivalent of 2-triphenylenecarboxylic acid from step b) is stirred with 2.0 equivalents of $BH_3$ THF in THF at room temperature for 16 hours. The reaction product is converted further after the aqueous workup in step f).

Step f)

The reaction product from step e) is reacted with $MnO_2$ (25.0 equivalents, based on 2-triphenylenecarboxylic acid) in $CHCl_3$ as a solvent under reflux for 3 days. After filtration through Celite, the reaction product is converted further in step g).

Step g)

The reaction product from step f) is stirred with 3.3 equivalents (based on 2-triphenylenecarboxylic acid) of $H_2NOH.HCl$ and 9.0 equivalents of NaOH in EtOH at room temperature for 1 hour and under reflux for 30 min. The reaction product (2-triphenylenealdoxime) obtained in 80-90% yield is converted further in step h) after the aqueous workup.

Step h)

The reaction product from step g) is stirred with 1.0 equivalent (based on 2-triphenylenealdoxime) of NCS in $CHCl_3$ for 30 min. Thereafter, the mixture is admixed with vinyl bromide (1.0 equivalent, based on 2-triphenylenealdoxime) and $NEt_3$ (1.1 equivalent) is added dropwise, to obtain, after stirring at room temperature for 12 hours and aqueous workup, the triphenylene derivative of the formula IIe. Alternatively to vinyl bromide, vinyl acetate or phenyl vinyl selenide can be used, in which case an additional refluxing step is added before the workup when vinyl acetate is used, while the use of vinyl selenide requires the addition of 30% $H_2O_2$ at 0° C. before the workup (in this case the refluxing step is dispensed with).

9. Preparation of the Inventive Triphenylene Derivatives of the Formula (IIa) According to Scheme 4

Step a)

Triphenylene (1 equivalent) is brominated with 8 equivalents of $Br_2$ in the presence of catalytic amounts of iron in nitrobenzene to obtain 80% brominated triphenylene derivative.

Step b)

The brominated triphenylene derivative (1 equivalent) is subsequently stirred with 5-10 mol % of CuI, 20 mol % of amine (N,N-dimethylcyclohexane-1,2-diamine or phenantroline), 1.0 equivalent of pyrazol and 2.1 equivalents of base ($K_2CO_3$, $CsCO_3$ or NaOtBu) at 110° C. in toluene for 24 hours.

Step c)

The reaction product obtained in step b) is subsequently converted to the triphenylene derivative of the formula IIf in step c1), in step c2) or in step c3):

$c_1$) iPrMgCl.LiCl; HCl; $c_2$) $H_2$, $NEt_3$, $Pd(OH)_2/C$; $c_3$) $HCO_2H$, $NEt_3$, $P(oTol)_3$, $Pd(OAc)_2$, DMF, 50° C., 24 h.

10. Preparation of the Inventive Triphenylene Derivatives of the Formula (IIa) According to scheme 5a 1-trifluoromethanesulfonato-2-trimethylsilylbenzene (3 equivalents) is reacted with 1 equivalent of the appropriate iodoaromatic (see scheme 5a), in the presence of 5 mol % of $Pd(OAc)_2$, 5 mol % of dppf and 4 equivalents of CsF in toluene/acetonitrile, to obtain the desired ligands of the formulae IId), IIe) and IIf).

The invention claimed is:

1. An organometallic complex of the general formula (I)

$$M[L_1]_q[L_2]_r[L_3]_s \qquad (I)$$

in which

M is a metal atom selected from the group consisting of Ir, Co, Rh, Ni, Pd, Pt, Fe, Ru, Os, Cr, Mo, W, Mn, Tc, Re, and Au;

$L_1$ is a monoanionic bidentate ligand based on a compound of the formula (IIa)

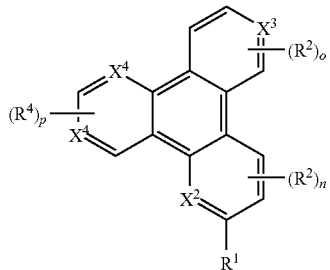

in which:
$R^1$ is a radical of the formula

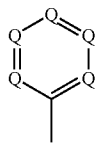

where Q is in each case independently $CR^a$ or N, where at least one Q group in an ortho-position to the bonding site is N and $R^a$ is hydrogen;
or a radical of the formulae

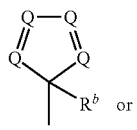  (a)

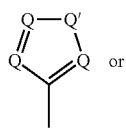  (b)

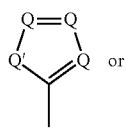  (c)

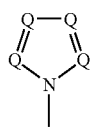  (d)

where Q is in each case independently $CR^a$ or N, where at least one Q group in an ortho-position to the bonding site is N, and Q' is $CR^a{}_2$, O, S or $NR^c$ and $R^b$ and $R^c$ are each independently hydrogen, alkyl, cycloalkyl, heterocycloalkyl, aryl, heteroaryl, amino, $CF_3$, CN, alkoxy or F;
wherein $R^1$ may optionally bear a fused group;
$R^2$, $R^3$, and
$R^4$ are each independently substituted or unsubstituted $C_1$-$C_{20}$-alkyl, substituted or unsubstituted $C_0$-$C_{20}$-alkylene-$C_3$-$C_{18}$-cycloalkyl, substituted or unsubstituted $C_0$-$C_{20}$-alkyleneheterocycloalkyl having 3-18 ring atoms, substituted or unsubstituted $C_0$-$C_{20}$-alkylene-$C_1$-$C_{20}$-alkoxy, substituted or unsubstituted $C_0$-$C_{20}$-alkylene-$C_6$-$C_{18}$-aryloxy, substituted or unsubstituted $C_0$-$C_{20}$-alkylene-$C_6$-$C_{18}$-aryl, or substituted or unsubstituted $C_0$-$C_{20}$-alkyleneheteroaryl having 5 to 18 ring atoms, wherein the substituent is $C_1$-$C_8$-alkyl, $C_1$-$C_8$ alkoxy, halogen, or pseudohalogen;
o is from 0 to 3, where the $R^3$ radicals, when o>1, may be the same or different;
p is from 0 to 2, where the $R^4$ radicals, when p>1, may be the same or different;
n is 0;
$X^2$ is N, CH or $CR^2$;
$X^3$ is N, CH or $CR^3$;
$X^4$ are each independently N, CH or $CR^4$;
$L_2$ is a mono- or dianionic ligand which may be mono- or bidentate;
$L_3$ is an uncharged mono- or bidentate ligand;
q is the number of ligands $L_1$, where q is 1, 2 or 3 and the ligands $L_1$, when q>1, may be the same or different;
r is the number of ligands $L_2$, where r is from 0 to 4 and the ligands $L_2$, when r>1, may be the same or different;
s is the number of ligands $L_3$, where s is from 0 to 4 and the ligands $L_3$, when s>1, may be the same or different;
and the sum of q+r+s depends on the oxidation state and coordination number of the metal used and on the denticity of the ligands $L_1$, $L_2$ and $L_3$ and also on the charge of the ligands $L_1$ and $L_2$.

2. The organometallic complex according to claim 1, wherein ligand $L_1$ has a triplet energy of 16 000 cm$^{-1}$ to 19 500 cm$^{-1}$.

3. The organometallic complex according to claim 1, wherein the radicals and indices in the triphenylene derivative of the formula (IIa) are each defined as follows:
$R^2$, $R^3$, and
$R^4$ are each independently $C_1$-$C_{20}$-alkyl, $C_0$-$C_{20}$-alkylene-$C_3$-$C_{18}$-cycloalkyl, $C_0$-$C_{20}$-alkyleneheterocycloalkyl having from 3 to 18 ring atoms, $C_0$-$C_{20}$-alkylene-$C_1$-$C_{20}$-alkoxy, $C_0$-$C_{20}$-alkylene-$C_6$-$C_{18}$-aryloxy, $C_0$-$C_{20}$-alkylene-$C_6$-$C_{18}$-aryl, $C_0$-$C_{20}$-alkyleneheteroaryl having from 5 to 18 ring atoms, where the aforementioned radicals are optionally substituted with $C_1$-$C_8$-alkyl, $C_1$-$C_8$ alkoxy, halogen or pseudohalogen;
o is from 0 to 3, where the $R^3$ radicals, when o>1, may be the same or different;
p is from 0 to 2, where the $R^4$ radicals, when p>1, may be the same or different;
n is 0;
$X^2$ is CH or $CR^2$;
$X^3$ is CH or $CR^3$; and
$X^4$ are each independently CH or $CR^4$.

4. The organometallic complex according to claim 1, wherein the metal atom M is selected from the group consisting of Ir, Rh, Pd, Pt, and Ru in any oxidation state possible for the corresponding metal atom.

5. The organometallic complex according to claim 1, wherein
M is Ir(III);
$L_2$ is a monoanionic bidentate ligand;
q is 1 or 2;
r is 1 or 2; and
s is 0
and the sum of q+r=3.

6. The organometallic complex according to claim 1, wherein $L_2$ is selected from the group consisting of β-diketonates, picolinate, amino acid anions and monoanionic bidentate ligands of the general formula (b)

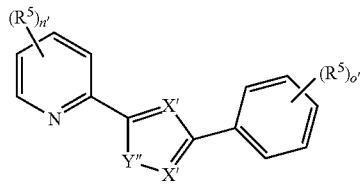

in which
R⁵ is hydrogen, $C_1$-$C_6$-alkyl, $C_0$-$C_4$-alkylene-$C_3$-$C_8$-cycloalkyl, or $C_0$-$C_4$-alkylene-$C_6$-$C_{18}$-aryl;
X' is N;
Y" is $N^-$;
n' is 1, 2, 3 or 4; and
o' is 1, 2, 3, 4 or 5.

7. A process for preparing organometallic complexes according to claim 1 by
 (a) reacting metal salts or metal complexes which comprise the desired metal M and optionally comprise one or more ligands $L_3$ with a first ligand $L_1$ or $L_2$ to give metal complexes which bear either one or more ligands $L_1$ or one or more ligands $L_2$, optionally in addition to one or more ligands $L_3$; and
 (b) reacting the metal complexes obtained in (a) with a second ligand $L_1$ when the metal complex obtained in (a) comprises one or more ligands $L_2$, or with a second ligand $L_2$, when the metal complex obtained in (a) comprises one or more ligands $L_1$, to obtain an organometallic complex of the formula (I), provided this reaction is dispensed with in the case that the organometallic complex of the formula (I) does not comprise any ligand $L_2$, or when r in the organometallic complex of the formula (I) is 0.

8. A mixture comprising at least one matrix material and at least one organometallic complex prepared according to claim 7.

9. A method of preparing an organic light-emitting diode, comprising providing an organometallic complex according to claim 1 in the organic light-emitting diode.

10. The method according to claim 9, wherein the organometallic complex is an emitter material.

* * * * *